(12) United States Patent
Delval et al.

(10) Patent No.: US 7,448,868 B2
(45) Date of Patent: Nov. 11, 2008

(54) TOOL HOLDER FOR FLEXIBLY-DEFORMABLE TOOL

(75) Inventors: Alain Delval, Brassus (CH); Yannic Rosset, Celigny (CH); Jean-Claude Volckmann, Ville-la-Grand (FR)

(73) Assignee: David Weill, Begnins (CH)

( * ) Notice: Subject to any disclaimer, the term of this patent is extended or adjusted under 35 U.S.C. 154(b) by 403 days.

(21) Appl. No.: 10/509,556

(22) PCT Filed: Apr. 2, 2003

(86) PCT No.: PCT/IB03/01192

§ 371 (c)(1),
(2), (4) Date: Sep. 29, 2004

(87) PCT Pub. No.: WO03/082387

PCT Pub. Date: Oct. 9, 2003

(65) Prior Publication Data

US 2005/0119612 A1   Jun. 2, 2005

(30) Foreign Application Priority Data

Apr. 2, 2002   (FR) .................................. 02 04093

(51) Int. Cl.
*A61C 17/00* (2006.01)
*A61C 3/00* (2006.01)
*A61M 5/32* (2006.01)
*B23B 5/22* (2006.01)

(52) U.S. Cl. .......................... 433/89; 433/147; 604/272; 279/5

(58) Field of Classification Search ............. 433/89–90, 433/80, 102, 147; 604/218, 272, 239–241, 604/243; 279/5–6; 140/123, 124, 149
See application file for complete search history.

(56) References Cited

U.S. PATENT DOCUMENTS

| | | | | |
|---|---|---|---|---|
| 1,993,398 A | * | 3/1935 | Cislak ........................ | 604/241 |
| 2,016,631 A |   | 10/1935 | Everett | |
| 2,531,893 A | * | 11/1950 | Roehr ........................ | 604/206 |
| 3,326,206 A | * | 6/1967 | Barr, Sr. et al. ............. | 600/577 |
| 3,534,476 A |   | 10/1970 | Winters | |

(Continued)

FOREIGN PATENT DOCUMENTS

FR   2 473 318   7/1981

(Continued)

*Primary Examiner*—John J Wilson
(74) *Attorney, Agent, or Firm*—Frommer Lawrence & Haug LLP; Ronald R. Santucci

(57) ABSTRACT

The invention relates to a tool holder (1) which is intended to receive a flexibly-deformable tool (12), such as an injection needle or a cutting tool. The operating direction (15) of the tool is not parallel to the axis (14) of the tool holder (1). The inventive tool holder (1) is characterised in that it ends in a part (4) of a channel that opens out onto the outside of the body (2) of the tool holder, comprising a surface having generatrices that are essentially parallel to the axis of the body and enabling the tool (12) to be introduced by moving same in relation to the axis (14) of the body of the tool holder. Said tool holder (1) comprises forms that enable the safe introduction of the needle, simple cleaning, inexpensive manufacture and a quality connection between the needle and the body.

9 Claims, 3 Drawing Sheets

U.S. PATENT DOCUMENTS

| | | | |
|---|---|---|---|
| 3,640,278 A * | 2/1972 | Friedman | 604/192 |
| 4,624,393 A * | 11/1986 | Lopez | 222/83.5 |
| 4,710,178 A * | 12/1987 | Henri et al. | 604/209 |
| 5,891,106 A * | 4/1999 | Butuzov et al. | 604/209 |
| 6,135,771 A * | 10/2000 | Dragan et al. | 433/90 |
| 6,200,296 B1 | 3/2001 | Dibiasi et al. | |
| 6,468,248 B1 * | 10/2002 | Gibbs | 604/164.01 |
| 7,077,830 B2 * | 7/2006 | Higaki et al. | 604/272 |

FOREIGN PATENT DOCUMENTS

| | | |
|---|---|---|
| FR | 2 535 206 | 5/1984 |
| FR | 2 556 595 | 6/1985 |
| FR | 2 785 813 | 5/2000 |
| GB | 682 372 A | 11/1952 |

* cited by examiner

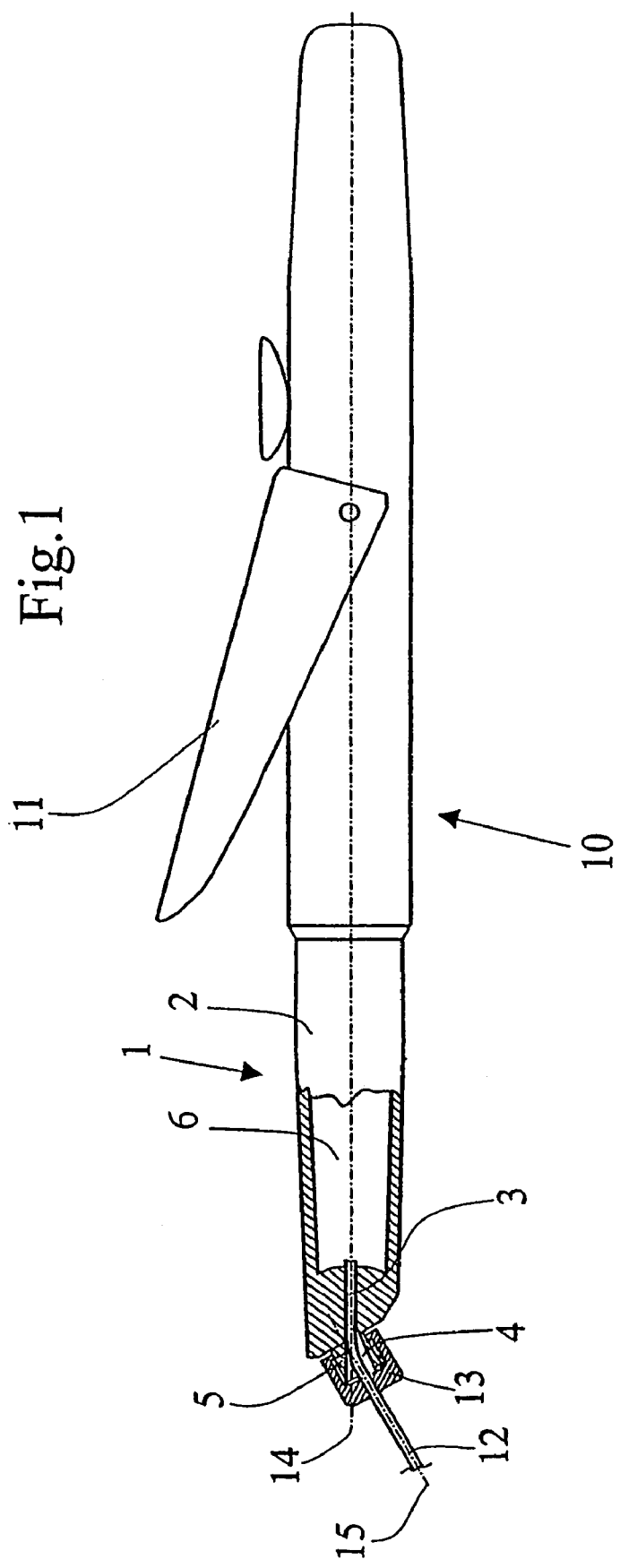

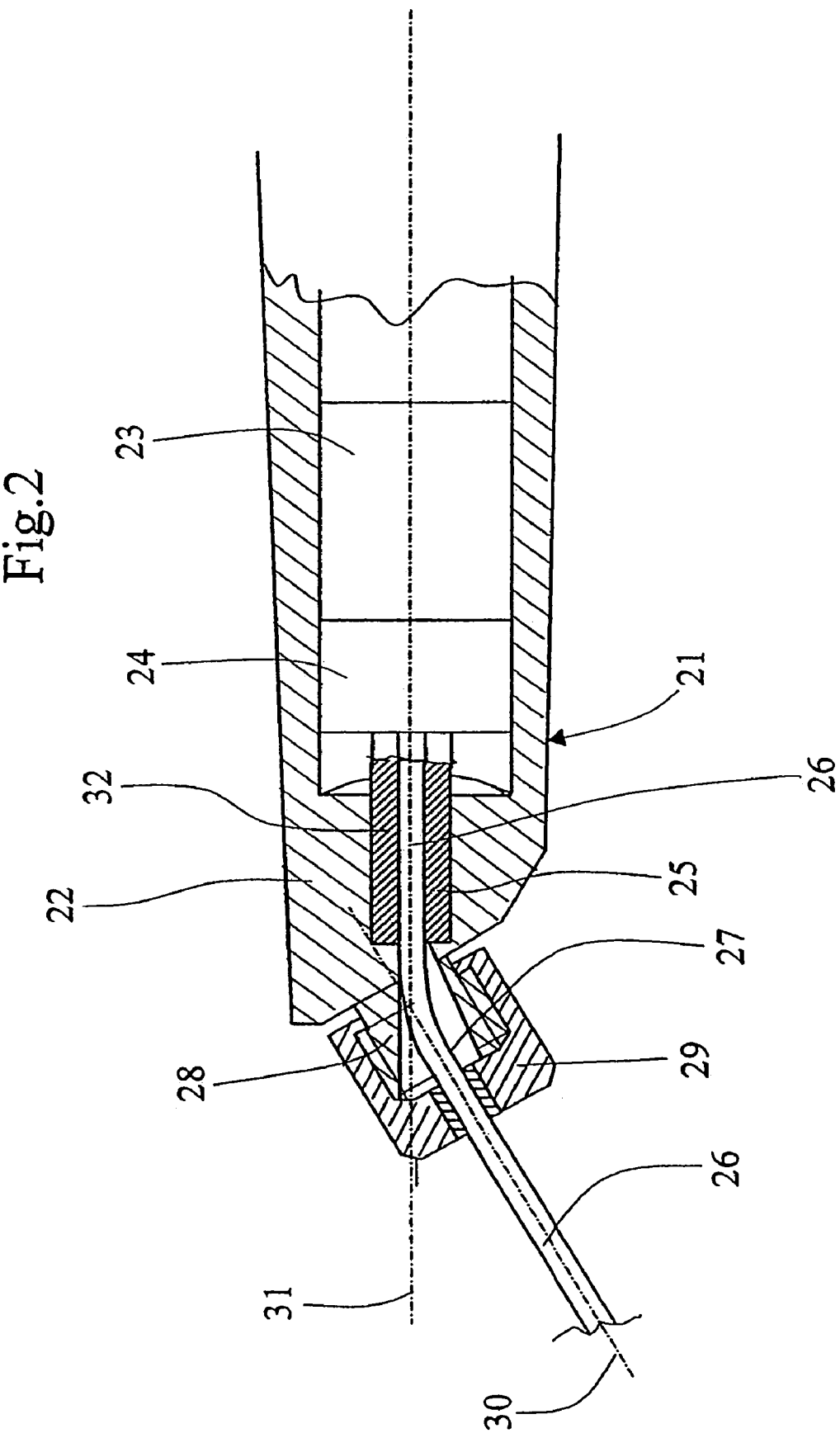

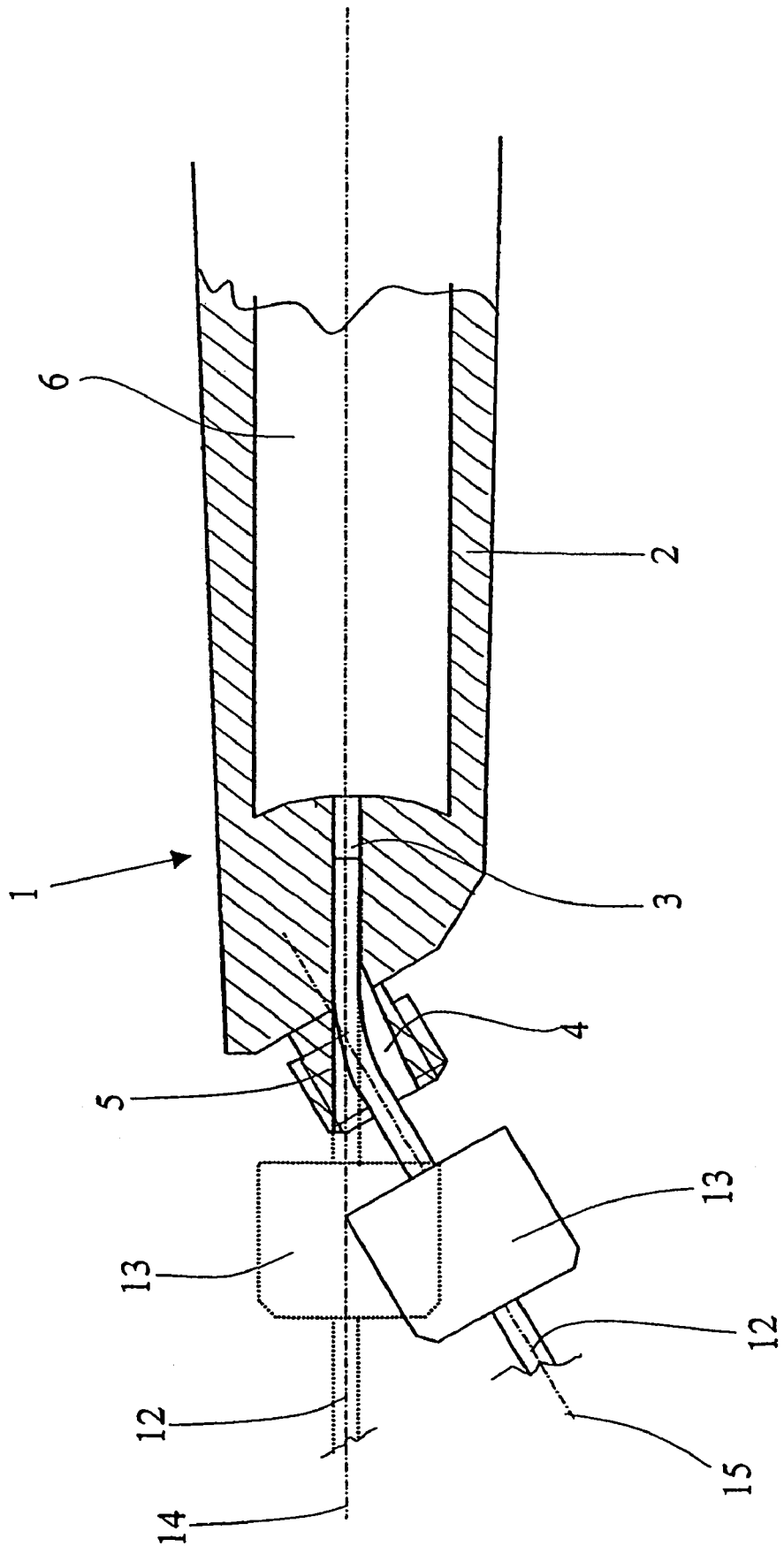

TOOL HOLDER FOR FLEXIBLY-DEFORMABLE TOOL

FIELD OF THE INVENTION

This application is a 371 filing of PCT/IB03/01192 filed Apr. 2, 2003 and published Oct. 9, 2003 under publication number WO 03/082387 and claims priority benefits of French Patent Application No. 02/04093 filed Apr. 2, 2002.

The present invention concerns a tool holder which is intended to receive a flexibly deformable tool. It concerns more precisely a tool holder defined according to the preamble of claim 1. The invention also concerns a device comprising such a tool holder and a flexibly deformable tool.

PRIOR ART

A dental syringe for intraligamentary injection is known from patent application FR 2 535 206. This syringe permits injection of product through a very fine and flexible needle into the ligaments situated between the jaw bone and the tooth. It is principally composed of an elongate body on which an injection control lever is articulated, a container holder housing a container filled with liquid to be injected, and an endpiece comprising the injection needle. In order to resolve problems of difficult access to the zones where the injections are to be given, the body of the syringe has an injection head which is at an angle to the axis of the body of the syringe. The removable needle is fitted on the body before performing the injections and is then withdrawn afterward. When fitting it in place, the needle is introduced into the syringe body parallel to the axis of the injection head, undergoing a flexion movement so that its end positions itself parallel to the axis of the container holder. A conical hole serves to guide the needle during its introduction and provides the stresses necessary for its flexion. The angle between the axis of the injection head and the axis of the syringe body being considerable, the needle introduced into the injection head comes into contact with a generatrix of the cone, forming too great an angle with it, and buckles. To overcome this problem, a certificate of addition application 2 556 595 to a French patent provides a channel which opens out at the end of the injection head and into the container holder. This channel permits guiding of the needle from its introduction into the injection head to its emergence into the container holder. However, this solution has disadvantages. First, the diameter of the needle and that of the channel being substantially the same, introduction of the needle into the channel is difficult, or even dangerous. Cases have been reported where the user has been injured through faulty introduction of the needle. Also, at the area where the needle is fixed to them, the syringes have zones which are difficult to clean and disinfect and thus difficult to sterilize. This applies particularly to the curved channel, the perimeter of the cone, and the rear of the injection head. Finally, production of a syringe comprising a curved channel is complicated and, consequently, expensive.

To overcome these problems, FR 2 785 813 discloses an injection syringe which, at the end of its body, has a channel intended to receive a needle, and with a conical part whose axis is parallel to the axis of the body and which widens toward the outside of the body. The needle is connected to an internally threaded ring screwed onto a threaded injection head which forms an angle with the axis of the body. This syringe has disadvantages. First, the conical part interferes with the threaded head so that the thread is nonexistent over a portion of the head. This detracts from the quality of the connection between the body and the needle. Also, when the needle is introduced in a direction parallel to one of the generatrices of the cone, the bevel at the end of the needle risks abutting against the opposite generatrix of the cone. This poses risks of injury to the user attempting to position the needle in the channel. Finally, the needle, once it has been curved in its operating direction, bears on one of the generatrices of the conical part and as a result risks being damaged. The reasons for this is that, in view of the quality of the surface of the conical part, the needle does not lie on the totality of a generatrix, during its movement of fixation to the body, but on several points. In view of the dimensions of the needle, the pressure exerted by these points on the needle poses a risk of damaging not only its outer part, but also its channel for injection of product. Such damage necessarily has consequences on the force that has to be applied to the syringe in order to inject the product it contains.

SUMMARY OF THE INVENTION

The invention relates to a tool holder comprising a body with a channel intended to receive the end of the tool, and variants thereof. The invention further comprises the tool holder and a flexibly deformable tool, and variants thereof. Finally, the invention comprises two alternative embodiments relating to additional variants of the tool holder and tool device.

The tool holder according to the invention is characterized by the characterizing part of claim 1.

Claims 2 through 7 define variants of the tool holder.

The device comprising such a tool holder and a flexibly deformable tool is defined by independent claim 8.

Claims 9 through 11 define variants of the device.

BRIEF DESCRIPTION OF THE DRAWINGS

Two embodiments of the invention, given as examples, are shown in the attached drawing.

FIG. 1 shows an overall view of a device according to the invention, comprising a tool holder and a flexibly deformable tool.

FIG. 2 shows a diagrammatic cross section of a tool holder according to the invention, receiving a cutting tool which is flexibly deformable elastically.

FIG. 3 is a cross section of the device according to the invention, the flexibly deformable tool being shown in two positions corresponding to two stages in the method of joining it to the tool holder.

DETAILED DESCRIPTION OF THE EMBODIMENTS

The device 10 shown in FIG. 1 is a syringe for injecting liquids or pastes. It comprises a tool holder 1 and a lever 11 acting on a mechanism (not shown) for controlling the displacement of a thrust cylinder which causes ejection of the liquid or paste through a needle 12. It should be noted that the needle 12 can either be flexibly deformable elastically or can be flexibly deformable beyond the elastic range of the material from which it is made. The tool holder 1 comprises a body 2 in which a reservoir 6 is formed which can directly receive the liquid or paste to be injected or a container filled with liquid or paste to be injected. At the bottom of the reservoir 6 a channel is formed which comprises a cylindrical part 3 parallel to the axis of the body 2. This channel 3 ends in a part 4 which is in the form of a divergent cone opening to the outside of the body 2 in the area of the support 5 of the injection needle 12. The support 5 is threaded, for example, and permits connection of the needle 12 to the body 2. The conical part 4 has the shape of a cone of revolution, of which one of the generatrices is substantially parallel to the axis of the cylindrical part 3 of the channel.

The needle 12 is connected to a ring 13 which, for example, has an internal thread allowing it to be joined to the support 5 of the body 2.

To assemble the needle 12 and the body 2, the needle 12 is introduced into the conical part 4. In order to ensure good penetration of the needle into the cylindrical part of the channel, the needle can in particular be pressed against the cone in the area of the generatrix parallel to the axis of the body. The needle is thus substantially parallel to the cylindrical part of the channel. The needle is then introduced into the cylindrical part 3 by means of a translational movement thereof in the axis 14 of the body 2. The needle 12 is then situated in the position shown by dotted lines in FIG. 3. This method of introducing the needle makes it possible to preserve its end penetrating into the body. Flexion of the needle 12 is then effected so as to bring its free end into the direction determined by the axis 15 of the support 5. The needle 12 is then situated in the position shown by solid lines in FIG. 3. The internally threaded ring 13 integral with the needle 12 is then screwed onto the support 5. During this action, the needle 12 penetrates a little farther into the channel 3. Thus, the needle is joined to the body in three stages:

a stage in which the needle is introduced into the channel, a stage involving flexion of the needle, a stage in which the needle is fixed to the body.

To remove the needle 12 from the body 2, the internally threaded ring 13 connected to the needle 12 is unscrewed from the support 5. As the needle is no longer held in position on the support 5, it can be withdrawn from the channel by means of a translational movement thereof in the axis 14 of the body 2.

By virtue of this method of assembly, the actions comprising introduction of the needle 12 into the body 2 and flexion of the needle 12 take place one after the other. They are independent and, consequently, are easier to perform.

It should be noted that the cone 4 can be replaced by any configuration ensuring that the needle can be guided toward the cylindrical part 3 of the channel by virtue of a surface whose generatrices are substantially parallel to the axis of this cylindrical part, and ensuring that the needle does not come into contact against this configuration during its stages of flexion and of fixing and when it is in its operating position.

In a second embodiment, the body 22 of the tool holder 21 is applied to a drilling, milling, hammering or vibrating device intended, for example, for the field of dental surgery. The body 22 of the tool holder 21 comprises a pneumatic motor 23 or an electric motor driving a speed-reducing gear 24 or speed-increasing gear. It can also comprise any type of transducer with which it is possible to set in motion, either directly or indirectly, the tool or the assembly consisting of the body and of the tool. The speed-reducing gear 24 or speed-increasing gear drives a spindle 25 which has an axis parallel to the body 22. The spindle 25 has a channel 32 passing through it and receiving a tool 26 which is flexibly deformable elastically, for example a drill bit or a hollow or solid milling cutter. The spindle 25 is in a pivot connection in the body 22. The tool 26 and the spindle 25 between them having a tight fit, the tool 26 is driven in rotation by friction.

The spindle ends in a divergent cone 27 opening out from the body 22 in the area of the support 28 of the tool 26. This support 28 is threaded and allows the tool 26 to be connected to the body 22. The cone 27 is a cone of revolution, of which one of the generatrices is substantially parallel to the axis of the spindle 25.

The tool 26 is connected by a pivot connection to a ring 29 for guiding it. This ring has an internal thread allowing it to be joined to the support 28 of the body 22.

To assemble the tool 26 and the body 22, the tool 26 is introduced into the cone 27, then into the spindle 25 by means of a translational movement thereof along the axis 31 of the body 22. Flexion of the tool 26 is then effected in such a way as to bring its free end into the operating direction of the tool as determined by the axis 30 of the support. Finally, the internally threaded ring 29 connected to the tool 26 is screwed onto the support 28. During this action, the tool 26 penetrates a little farther into the channel 32 of the spindle 25.

To remove the tool 26 from the body, the internally threaded ring 29 is unscrewed from the support 28. As the tool 26 is no longer held in position on the support, it returns to its initial rectilinear position by virtue of its elastic characteristics. Finally, the tool 26 is withdrawn from the spindle 25 by means of a translational movement thereof along the axis 31 of the body 22.

A variant of this second embodiment differs from said second embodiment in that the device comprises an injection needle instead of the cutting tool and in that it comprises, in place of the motor 23 and the speed-reducing gear 24, a device permitting orientation of the needle in rotation about its axis, for example alternately, thus making it possible to position the bevel of the needle with respect to the surface to be penetrated in order to perform the injection. Such a device for orientation of a needle is described for example in patent application FR 2 473 318.

In the two embodiments described above, the tool is fitted in the body of the tool holder by screwing. However, this can be done by any other known means, for example a bayonet-type connection or shape-fit connection. Depending on the means of fixing used, the movement of the needle with respect to the body is different during the stage in which it is fixed to the body.

The invention claimed is:

1. A device comprising a tool holder and a flexibly deformable tool, the tool holder comprising:

an elongate body with a channel parallel to the body intended to receive the end of the tool; and a support at the end of the tool holder having an end part of the channel opening to the outside of the body, widening toward the outside of the body and configured to guide the tool toward the cylindrical part when it is being fitted in the tool holder, this part opening to the outside of the body comprising a surface of which one of the generatrices being substantially parallel to the axis of the cylindrical part of the channel and which extends from the cylindrical part to outside of the body, permitting introduction of the tool into the body by a displacement along the axis of the cylindrical part of the channel; and means to hold the tool after its flexion in such a way that at least a portion of the axis of the tool is in a direction not parallel to the axis of the body, the means being fixed to the support in the direction not parallel to the axis of the body.

2. The device as claimed in claim 1, wherein the part opening to the outside of the body has configurations allowing it to avoid contact with the tool during its stages of flexion and fixation and when said tool is in the operating position.

3. The device as claimed in claim 1, wherein the means for holding the tool in position comprise, on the body, a threaded end onto which an internally threaded ring connected to the tool is screwed.

4. The device as claimed in claim 1, wherein the means for holding the tool in position comprise, on the body, an end which cooperates with a ring connected to the tool in order to form a bayonet-type connection system.

5. The device as claimed in claim 1, wherein the means for holding the tool in position comprise, on the body, clip means which cooperate with complementary clip means on a ring connected to the tool.

6. The device as claimed in claim 1, wherein the means for holding the tool in position comprise, on the body, shape-fit means which cooperate with complementary shape-fit means on a ring connected to the tool.

7. The device comprising the tool holder as claimed in claim 1 and the flexibly deformable tool connected to a ring.

8. The device as claimed in claim 7, wherein the tool is connected to the ring by a pivot connection.

9. The device as claimed in claim 7, wherein the tool is an injection needle.

* * * * *